(12) United States Patent
Krier et al.

(10) Patent No.: US 10,070,510 B2
(45) Date of Patent: Sep. 4, 2018

(54) METHOD AND SYSTEM FOR CONTROLLING ION BEAM PULSES EXTRACTION

(71) Applicant: Ion Beam Applications S.A., Louvain-la-Neuve (BE)

(72) Inventors: Gabriel Krier, Court-St-Etiene (BE); Sèbastien Henrotin, Watermael-Boitsfort (BE); Yves Claereboudt, Nil-Saint-Vincent (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 15/725,350

(22) Filed: Oct. 5, 2017

(65) Prior Publication Data

US 2018/0098413 A1   Apr. 5, 2018

(30) Foreign Application Priority Data

Oct. 5, 2016 (EP) .................................. 16192454

(51) Int. Cl.
*G21G 5/00* (2006.01)
*H05H 13/00* (2006.01)
(Continued)

(52) U.S. Cl.
CPC .......... *H05H 13/02* (2013.01); *A61N 5/1043* (2013.01); *H05H 7/001* (2013.01); *H05H 7/02* (2013.01);
(Continued)

(58) Field of Classification Search
CPC . H05H 13/02; H05H 7/02; H05H 7/04; A61N 5/1043
See application file for complete search history.

(56) References Cited

U.S. PATENT DOCUMENTS

| 2009/0140671 A1* | 6/2009 | O'Neal, III | H03L 7/00 315/502 |
| 2009/0236545 A1* | 9/2009 | Timmer | A61N 5/10 250/492.1 |

(Continued)

FOREIGN PATENT DOCUMENTS

| EP | 2446718 A1 | 5/2012 |
| WO | WO 2010/149740 A1 | 12/2010 |

OTHER PUBLICATIONS

European Search Report for International Application No. EP 16192454.3 from the European Patent Office, dated Feb. 10, 2017.

*Primary Examiner* — Douglas W Owens
*Assistant Examiner* — Raymond R Chai
(74) *Attorney, Agent, or Firm* — Finnegan, Henderson, Farabow, Garrett & Dunner LLP

(57) ABSTRACT

The embodiments of the present disclosure relate to a method and system for controlling the extraction of ion beam pulses produced by a synchrocyclotron. The synchrocyclotron comprises electrodes configured to be placed in a magnetic field. An alternating voltage is applied between the electrodes, and the frequency of the alternating voltage is modulated in a cyclic manner. In other embodiments, the method further comprises the steps of starting an acceleration cycle of the synchrocyclotron, generating a reference signal when the modulated frequency reaches a predefined value, communicating the time, at which the reference signal is generated, to the beam control elements, assessing one or more status parameters of the one or more beam control elements, and cancelling or proceeding with the extraction of the beam pulse depending on the results of the assessment.

20 Claims, 4 Drawing Sheets

(51) Int. Cl.
*H05H 13/02* (2006.01)
*H05H 7/02* (2006.01)
*H05H 7/04* (2006.01)
*H05H 7/00* (2006.01)
*A61N 5/10* (2006.01)

(52) U.S. Cl.
CPC ....... *H05H 7/04* (2013.01); *A61N 2005/1087* (2013.01); *H05H 2007/008* (2013.01); *H05H 2007/022* (2013.01); *H05H 2007/025* (2013.01); *H05H 2007/046* (2013.01); *H05H 2277/10* (2013.01)

(56) References Cited

U.S. PATENT DOCUMENTS

| | | | |
|---|---|---|---|
| 2014/0152199 A1* | 6/2014 | Arita | H05H 13/04 315/503 |
| 2015/0090894 A1* | 4/2015 | Zwart | A61N 5/10 250/396 ML |
| 2015/0283404 A1* | 10/2015 | Okazaki | A61N 5/1077 600/1 |
| 2016/0213950 A1* | 7/2016 | Ebina | A61N 5/1048 |

* cited by examiner

METHOD AND SYSTEM FOR CONTROLLING ION BEAM PULSES EXTRACTION

CROSS-REFERENCE TO RELATED PATENT APPLICATIONS

This application claims the benefit of a European Application No. EP 16192454.3, filed Oct. 5, 2016, which is hereby incorporated by reference in its entirety.

FIELD OF THE INVENTION

The invention generally relates to a method and system for controlling the extraction of an ion beam pulse in a synchrocyclotron.

BACKGROUND OF THE INVENTION

Beams of charged particles are used in medical application for cancer treatment when cancerous cells are localised within a specific region of the patient's body. Recent techniques allow for a precise extraction of a given dose of radiation in a target volume of the patient. Charged particle therapy systems usually comprise a particle accelerator for producing a beam of charged particles and beam extraction means. The means for extracting the ion beam may comprise beam deflecting means such as magnets, energy degraders, etc.

A charged particle therapy system is for example described in document EP 2446718. This document generally relates to a pulsed beam particle accelerator which can be used for particle radiation therapy. More particular, a device and method are provided to control the number of particles within a beam pulse to irradiate an irradiation spot in a target volume. The particle accelerator comprises means for varying the number of particles within each beam pulse of the pulsed ion beam from a minimum value to a maximum value as a function of the value of a beam control parameter. For each particle irradiation the required number of particles for each beam pulse is controlled by defining a value for the beam control parameter based on calibration data.

In order to irradiate a specific irradiation spot in a target volume, beam control elements such as scanning magnets and/or an energy degrader are generally used. The setting of the beam control elements may take place in between subsequent particle pulses of the beam, for example. The operation of a synchrocyclotron for particle radiation therapy however also requires an assessment of the status of the beam control elements before allowing the departure of a bunch of particles from the accelerator. This assessment must be done within the time available between bunches, and for some beam control elements, the assessment is done preferably as late as possible, in order to allow the setting of the beam control elements a maximum of time. On the other hand, the assessment must be finished fast enough so that cancellation of the beam is still possible. Due to deviations from the theoretical frequency cycle of the synchrocyclotron, for example because of imperfections in the rotating capacitor used for generating the cycle, presently known systems do not allow to ensure that all assessment steps are concluded in time, because the beam control elements have no way of taking the cycle deviations into account. This results in ineffective system operation, for example involving the extraction of a bunch despite a negative assessment of the status of a number of beam control elements.

SUMMARY OF THE INVENTION

The invention is related to a method and apparatus as disclosed in the appended claims. The invention is firstly related to a method for controlling the extraction of ion beam pulses produced by a synchrocyclotron, the synchrocyclotron comprising electrodes configured to be placed in a magnetic field, wherein an alternating voltage is applied between the electrodes, and wherein the frequency of the alternating voltage is modulated in a cyclic manner, the method applying one or more beam control elements, the method comprising:

starting an acceleration cycle of the synchrocyclotron to provide an ion beam pulse, wherein one modulation cycle of the modulated frequency of the alternating voltage corresponds to one acceleration cycle of the synchrocyclotron;

characterized in that the method further comprises:

generating a reference signal based on a measurement of the frequency of the alternating voltage applied during an acceleration cycle, the reference signal being generated when the frequency reaches a predefined value;

communicating the time, at which the reference signal is generated, to the one or more beam control elements, assessing one or more status parameters of the one or more beam control elements, wherein the assessment is synchronised with the generation of the reference signal;

cancelling or proceeding with the extraction of the beam pulse depending on the results of the assessment.

According to an embodiment, the method further uses one or more beam monitoring elements, wherein the time at which the reference signal is generated is communicated to said beam monitoring elements, and wherein reading the output of the one or more beam monitoring elements is equally synchronized with the generation of the reference signal.

According to an embodiment, the cancellation of the beam pulse comprises lowering the magnitude of the alternating voltage between the electrodes of the synchrocyclotron.

According to an embodiment, the one or more beam control elements are interconnected in a network, and wherein the step of communicating the time comprises sending a timestamp over the network, to the one or more beam control elements and if applicable, to the one or more beam monitoring elements.

As an alternative to the latter embodiment, the step of communicating the time may comprise propagating the reference signal, over one or more cables, to the respective one or more beam control elements and if applicable, to the one or more beam monitoring elements.

According to an embodiment, the frequency changes according to a cyclic pattern comprising a rising slope and a falling slope, and wherein the generation of the reference signal occurs when the frequency is on the rising slope.

According to an embodiment, the synchrocyclotron comprises a rotating capacitor for modulating the frequency of the alternating voltage applied between the electrodes.

According to an embodiment, the reference signal is generated when the frequency of the alternating voltage applied between the electrodes reaches a given value between 60 MHz and 92 MHz.

The reference signal may be generated at selected cycles of the frequency of the alternating voltage.

According to an embodiment, the one or more beam control elements comprise at least one beam control element external to the synchrocyclotron. Said external beam control elements may comprise at least a set of scanning magnets for directing the beam at one or more particular portions of a target.

According to an embodiment, the operation of the one or more beam control elements, and if applicable, the one or more beam monitoring elements, is synchronized according to a common timeline.

The invention is equally related to an ion beam irradiation system configured to control the extraction of ion beam pulses by the method according to the invention, comprising:
- a synchrocyclotron,
- one or more beam control elements,
- one or more beam monitoring elements,
- a central control unit,
- an antenna for detecting the frequency of the alternating voltage between the electrodes of the synchrocyclotron,
- a reference signal generator.

According to an embodiment of the ion beam irradiation system of the invention, the reference signal generator comprises:
- a digital sampler, for sampling a signal produced by the antenna,
- a computer for calculating the frequency of the alternating voltage on the basis of samples provided by the sampler, and configured to perform this calculation repeatedly during a frequency cycle of the modulated frequency,
- a controller for detecting when the calculated frequency is equal to a reference value, and for emitting the reference signal.

In the system according to the invention, said one or more beam control elements may comprise one or more of the following: scanning magnets, guiding magnets, an energy degrader.

BRIEF DESCRIPTION OF THE DRAWINGS

By way of example, preferred, non-limiting embodiments of the invention will now be described in detail with reference to the accompanying drawings, in which.

DETAILED DESCRIPTION OF ONE OR MORE PREFERRED EMBODIMENTS

Figure 1:
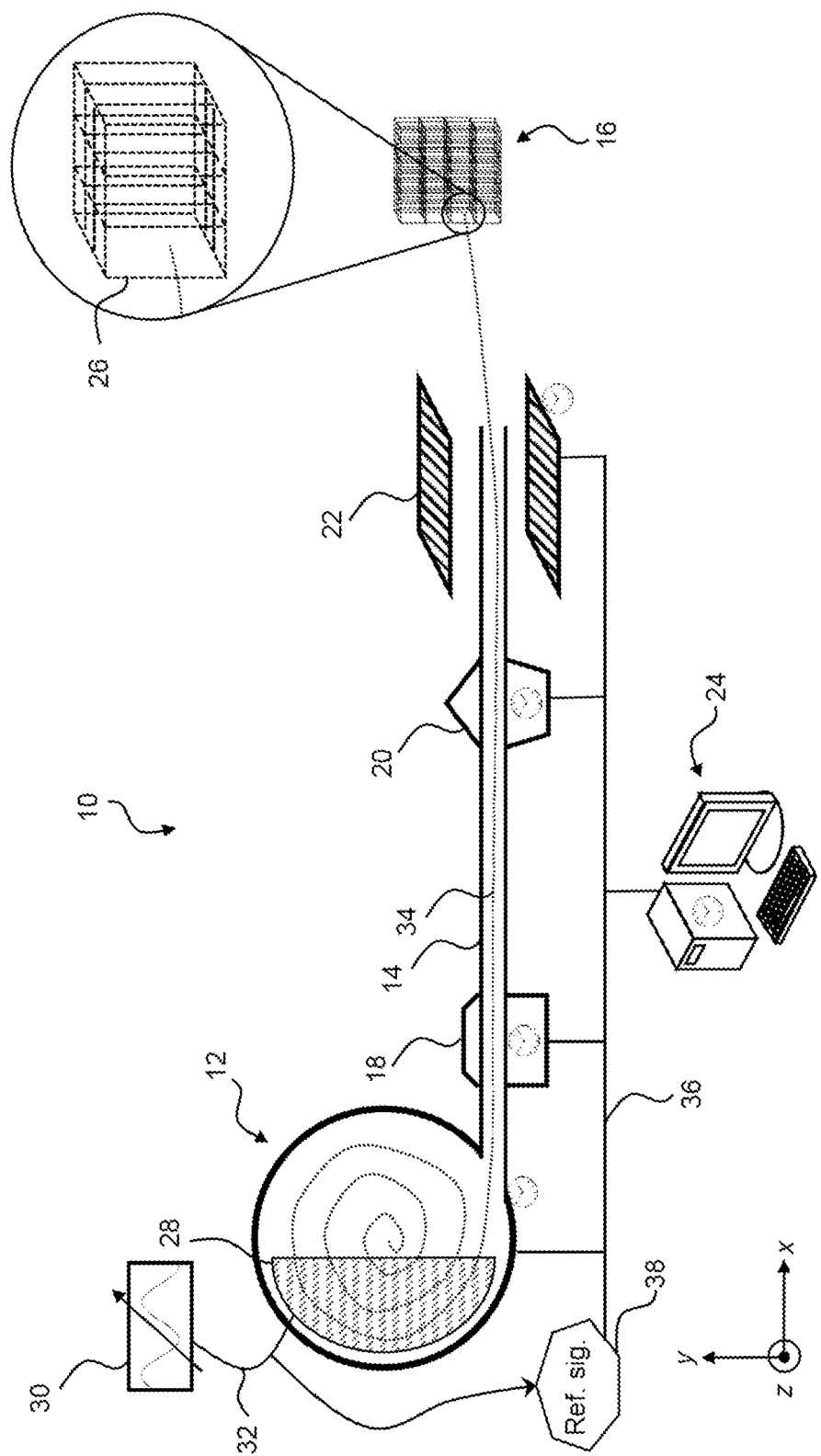
FIG. 1: is a simplified representation of an ion beam irradiation system according to an aspect of the invention.

FIG. 1 shows an ion beam irradiation system 10 comprising a synchrocyclotron 12, beam transport means 14 for propagating the beam from the synchrocyclotron 10 to the patient 16, beam controlling or monitoring elements 18, 20, 22 and a central control unit 24. The ion beam irradiation system 10 is configured to deliver irradiation doses to a target 16 within a patient's body according to an irradiation plan that is encoded in the central control unit 24. The central control unit 24 is thus a component that is known as such in the state of the art. However according to some embodiments of the invention, this central control unit may additionally be configured to perform particular steps of the method of the invention, as will be described further in this description. The different elements constituting the ion beam irradiation system 10 will be described in the following.

The synchrocyclotron 12 accelerates charged particles (ions) that are in a vacuum chamber using an alternating voltage which is applied between two electrodes. This may be two hollow "D"-shaped electrodes 28 (Dees, only one Dee is shown in FIG. 1). The Dees 28 face each other and are separated by a gap, creating a cylindrical space within them for the charged particles to move. The charged particles are injected into the centre of this space by a source of charged particles (e.g. protons). The Dees 28 are located between the poles of a large electromagnet which applies a static magnetic field B perpendicular to the electrode plane (perpendicular to the x-y plane, i.e. in the z-direction). Due to the force applied by the magnetic field and the electric field to the moving charged particles (Lorentz force), the motion of charged particles describes a (semi-)circle in the x-y plane, thereby passing several times in alternating directions in the zone between the Dees 28. The particles are accelerated, i.e. the absolute value of the speed is increased, by the alternating voltage between the Dees 28. For an effective acceleration of the charged particles, the frequency of the alternating voltage should be chosen as the resonance frequency of the synchrocyclotron 12. The resonance frequency $f_r$ for the charged particles reads $f_r=q|B|/(2\pi m\gamma)$, where q is the charge of the ions, m is the rest mass of the ions, $\gamma=\gamma(v)$ is the Lorentz factor, v is the speed of the charged particles, B is the magnetic field and |B| its magnitude. Since the resonance frequency is related to the increasing relativistic mass 'mγ' of the charged particles, the resonance frequency decreases as the particle gains mass when it approaches the speed of light. In order to maintain the acceleration of the particle, the frequency of the alternating voltage is modulated cyclically, i.e. according to a sequence of rising and falling slopes. At the start of the falling slope of the frequency, a bunch of particles is captured and travels on a series of revolutions within the synchrocyclotron 12, while being accelerated at each transition between the Dees 28, timed with the modulated frequency of the alternating voltage. At a point near the end of the falling slope, the bunch of particles is extracted and directed at the target 16. This constitutes one ion beam pulse. Subsequent bunches of particles are captured, accelerated and extracted in this way, resulting in a sequence of ion beam pulses, hereafter referred to as a pulsed ion beam, issuing from the synchrocyclotron 12. Preferably, the acceleration cycle of the synchrocyclotron 12 lasts between 0.5 ms and 1.5 ms thereby providing an ion beam pulse every 0.5 ms to 1.5 ms.

The frequency required by the synchrocyclotron 12 to effectively accelerate the ions during an acceleration cycle is provided through a transmission line 32 and generated by a radiofrequency system 30, comprising a rotating capacitor (RotCo). The radiofrequency system 30 is electrically comparable to—or electrically modelled by—an RLC circuit (resistor, inductor, capacitor), where the resistor R models the resistive losses, the inductor L models the transmission line 32 and the capacitor C models the capacity resulting from the space between the radiofrequency system 30 and the ground. By including a RotCo in the RLC circuit, it is possible to tune the resonance frequency of the equivalent RLC circuit by cyclically modulating the capacity C, so that the frequency of the alternating voltage between the Dees 28 of the synchrocyclotron 12 is effectively modulated according to the rising and falling slopes as described above. For details about the RotCo and its implementation, see patent application US 2014/0103839.

Before the treatment of the patient begins, an irradiation plan is devised either on site or remotely by medical staff. The plan comprises a set of high level commands such as, for example, the amount of radiation (dose) in a particular unit volume 26 (a "voxel") of a 3D target area such as a tumor. The irradiation plan is then processed, on site, to low level commands comprising commanding setpoint values (hereinafter "setpoints") for the beam control elements 20, 22. These low level commands are encoded in the central control unit 24. For example, the setpoints may comprise target currents for the scanning magnets 22. Setpoints may also be defined independently from the irradiation plan.

A typical trajectory 34 of one bunch of ions of a pulsed ion beam is shown in FIG. 1. In the synchrocyclotron 12, the trajectory of the ions describes semi-circles with increasing radii over time. After that, the ions are extracted and propagate through beam transport means 14 towards the target voxel 26 defined in the irradiation plan. During their propagation through the beam transport means 14, beam control elements comprising an energy degrader 20 for adjusting the energy of the ion beam and a set of scanning magnets 22 for deflecting the ion beam in order for the beam to arrive at a desired position in a plane transverse to the propagation of the ion beam act on the ion beam. The energy degrader 20 is configured for tuning the depth (longitudinal direction) at which the major part of the radiation will be delivered. In other words, tuning the beam energy thanks to the energy degrader allows to tune the depth of the Bragg peak (i.e. the depth where most radiation will be absorbed by the patient). The beam transport means itself may be equipped with guiding magnets (not shown) such as, for example, dipole magnets for bending the ion beam or quadrupole magnets for focusing the beam. The guiding magnets, the energy degrader and the scanning magnets are examples of 'external beam control elements', i.e. beam control elements which are external to the synchrocyclotron 12. Beam control elements which are internal to the synchrocyclotron 12 are for example elements for regulating the arc current of the ion source, or for regulating the amplitude of the voltage applied between the Dees 28.

A passive beam monitoring element 18 is also shown in FIG. 1, which may be an ionization chamber 18 configured to measure the total charge of one or more ion beam pulses in order to determine an associated dose of radiation. The energy degrader 20 and scanning magnets 22 are configured to precisely tune the energy and the end trajectory of the ion beam pulse in order to irradiate the target voxel 26. Each of the external and internal beam control elements and the passive beam monitoring element comprise their own local control unit comprising an internal clock (depicted in FIG. 1 by clocks). The local control units of the beam control elements are configured to receive the low level commands based on the irradiation plan from the central control unit 24, and to set the beam control elements in accordance with said low level commands. For example, the control unit of the degrader 20 comprises an actuator for positioning the degrader element with respect to the target 16. The local control units of the beam control elements are furthermore configured to send back signals to the central control unit 24 which signals represent a status parameter of the beam control elements. The status of a beam control element is defined by the values of its status parameters. For example, the degrader element's control unit sends out a signal that is representative of the position of the degrader element (in that case one status parameter defines the status of the energy degrader element). The passive beam monitoring elements are also provided with a local control unit equipped to send a signal related to a measured value (e.g. a measured charge). However these control units are not equipped to modify the setting of the passive elements. The status of the one or more beam control elements may comprise one or more measured values of status parameters to be compared to the low level commands or setpoints preferably derived from the irradiation plan. In one embodiment of the invention, the measured values of the one or more beam control elements comply with the low level commands or setpoints if they are equal up to a predefined tolerance. In another embodiment, the compliance of the status may be much more complex. For example, a weight function may be employed to associate a specific weight to a particular beam control element (e.g. to the scanning magnets). It will be appreciated that there are a multitude of ways to check if the status of the one or more beam control elements comply with the setpoints.

All the components of the ion beam irradiation system 10 (e.g. the synchrocyclotron 12, the beam control elements 20, 22, the passive beam monitoring element 18 and the central control unit 24) have to work in concert during the acceleration cycle in order to achieve the goals of—and not deviate from—the setpoints. A precise synchronisation of the operation of all the components is therefore mandatory: the clocks depicted in FIG. 1 are synchronized so that all components, including all the beam control elements 20, 22 and the passive beam monitoring element 18, are operated according to a common timeline. This can be achieved in a number of ways as will be described further in this description. According to the invention, the generation of a reference signal 38 is added to this synchronization. The reference signal is generated on the basis of a measurement of the cyclically modulated frequency of the alternating voltage between the electrodes of the synchrocyclotron. In other words, when this frequency reaches a predefined value, preferably during the rising slope of the cycle, the reference signal 38 is generated. The time at which the reference signal 38 is generated is transmitted to the beam control elements 20, 22 and the passive beam monitoring element 18, so that a well-defined point of the cycle is known to all the beam control elements and the passive beam monitoring element. This allows the assessment procedures of these elements to be perfectly synchronized with the frequency cycle, even when this cycle deviates from the theoretical cycle, due to imperfections in the RotCo for example. The assessment of a number of external beam control elements 20, 22, in particular the scanning magnets 22, may be performed at a point in time during the cycle that is very close to the point where a bunch of ions is to be extracted. In this way, a maximum of time is given for the external beam control elements to reach a given setpoint. At the same time, because the timing is accurately defined with respect to the reference signal, cancellation of the beam remains possible when the assessment proves that a given setpoint is not reached. Cancellation of the beam is indeed not possible at any time during the acceleration cycle of the synchrocyclotron. The cancellation procedure will be described in more details in the following. Assessment of internal beam control elements may be performed in the same way, in as far as this control is possible during the acceleration cycle.

Figure 2:
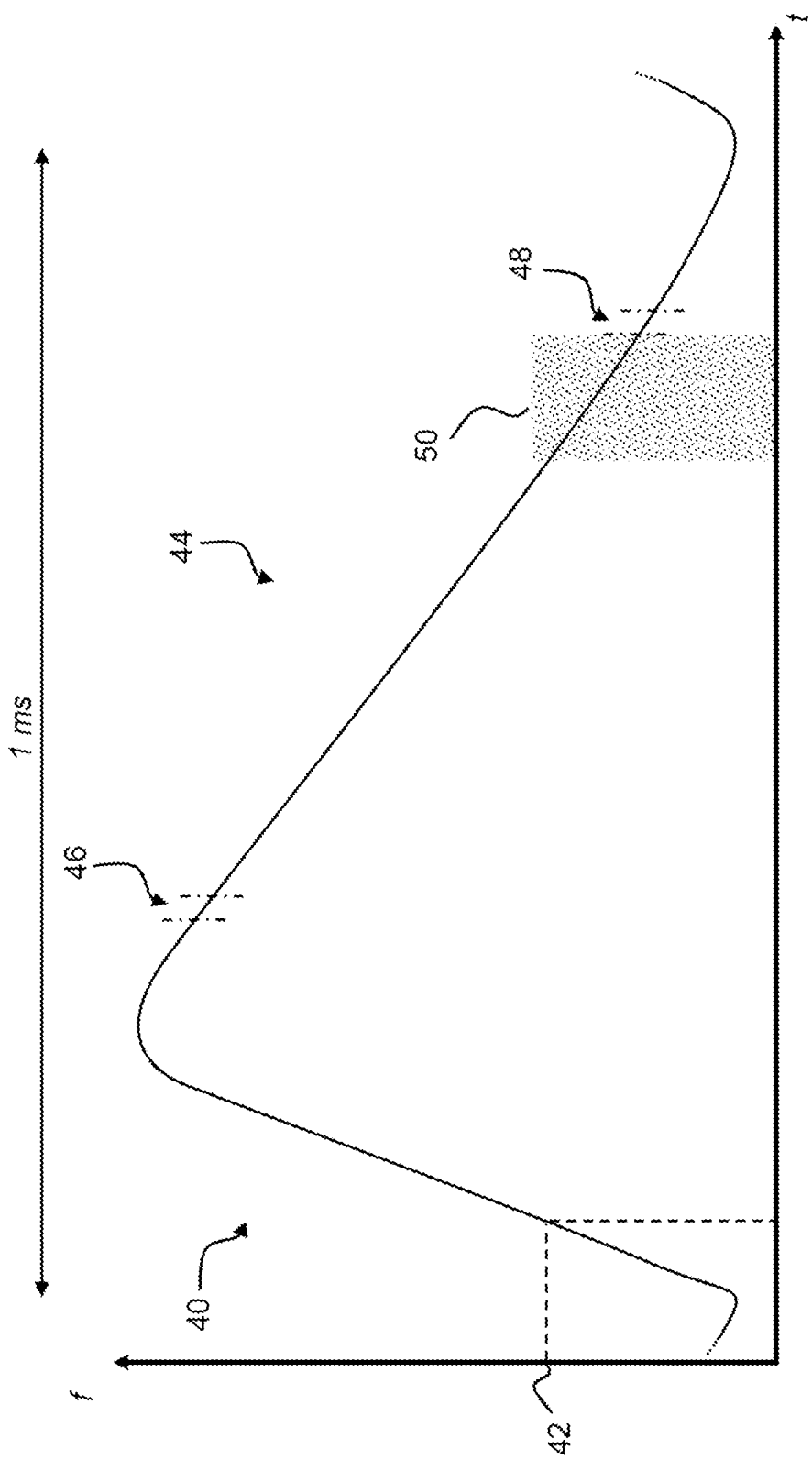
FIG. 2: depicts the frequency of the alternating voltage during one acceleration cycle of the synchrocyclotron.

FIG. 2 shows the frequency of the alternating voltage applied to the Dees as a function of time for one acceleration cycle of the synchrocyclotron. One acceleration cycle is corresponding to one modulation cycle of the modulated frequency of the alternating voltage. In the exemplary case of FIG. 2, the acceleration cycle lasts about 1 ms and comprises a rapid increase 40 of the frequency of the voltage between the Dees. After the rapid increase 40, the frequency decreases 44 more slowly. Shortly after the start of the decrease of the frequency, a bunch of ions is captured during a capture window 46 (i.e. the frequency applied to the Dees is the resonance frequency of the synchrocyclotron for ions moving at low speed v<<c). As explained before, the frequency of the alternating voltage continues to decrease in order for the resonance condition to be met between the capture of the ion beam and its extraction. Towards the end of the acceleration cycle, the ion beam pulse is extracted from the synchrocyclotron during an extraction window 48. The acceleration cycle is repeated in a cyclic pattern in order to provide a plurality of ion beam pulses. The reference signal is generated when the frequency reaches a predefined value either on the rising or the falling slope of the frequency cycle (not on both). Preferably the signal is generated on the slope that has the highest rate of change. In the embodiment of FIG. 2 this is the rising slope 40: the reference signal is generated when the frequency reaches a value 42 on this rising slope of the frequency cycle.

The frequency is measured with an RF antenna that is known per se in the art of (synchro)cyclotrons. According to a preferred embodiment, the electrical signal received from the antenna is then fed to a digital sampling unit and sampled at a sampling frequency that is sufficiently higher than the highest RF frequency generated by the Rotco-system, so that the frequency can be monitored throughout the acceleration cycle. The RF signal can for example be sampled, resulting in a number of sample values $y_0$ to $y_n$, taken during one or a few periods of the RF signal. From these values, the frequency and the amplitude of the RF signal can be solved using a suitable fitting algorithm. This algorithm is applied continuously during the acceleration cycle of the synchrocyclotron, yielding successive determinations of the frequency. When the frequency reaches the reference value 42, this triggers the generation of the reference signal. The means to generate the reference signal 38 in the above manner is referred to here as a reference signal generator, which may comprise a digital sampler and a computer needed to perform the fitting algorithm as well as a controller needed to assess when the reference frequency is reached, and emit the reference signal. The reference signal generator can be brought to practice in any suitable manner known in the art of signal processing and process control technology.

The cancellation of an ion beam pulse must follow strict rules in order to be sure that when a cancellation order is issued, the patient does not receive the dose of radiation in preparation in the synchrocyclotron. The person skilled in the art can determine the length of a time interval 50 (a "forbidden time interval") finishing at the extraction of the ion beam pulse where a cancellation order of the ion beam pulse would result in an unwanted and/or uncontrolled irradiation of the patient. In one embodiment, the forbidden time interval could last approximately 80 µs. The cancellation order of the ion beam pulse must therefore be issued before this time interval 50. In order to realize a "clean" cancellation or stop of the pulse in preparation (i.e. prevent the patient from receiving the ion beam pulse), the cancellation order from the beam control system has to be issued before the forbidden time interval 50. The reference signal generated according to the invention ensures that the time between the generation of this reference signal and the start of the forbidden zone is always precisely known. This allows to design and program the various assessment procedures of the beam control elements in such a way that they are concluded before the start of the forbidden zone. Unwanted beam extraction and delivery to the patient because of untimely verification procedures is thereby avoided.

According to the embodiment illustrated in FIG. 1, all the components of the beam irradiation system 10 are interconnected in a network 36 (preferably an Ethernet network). The synchronisation of the internal clocks is achieved by the Precision Time Protocol (PTP, as known in the art). The PTP protocol achieves, on a local area network, a clock accuracy in the sub-microsecond range. In other words, all the components of the ion beam irradiation system 10 share the same and unique timeline. When the reference signal 38 is generated upon reaching the predefined frequency value 42, a timestamp indicating the time at which the signal has been generated is transmitted over the network to the various control units of the beam control elements and the passive monitoring elements.

Figure 3:
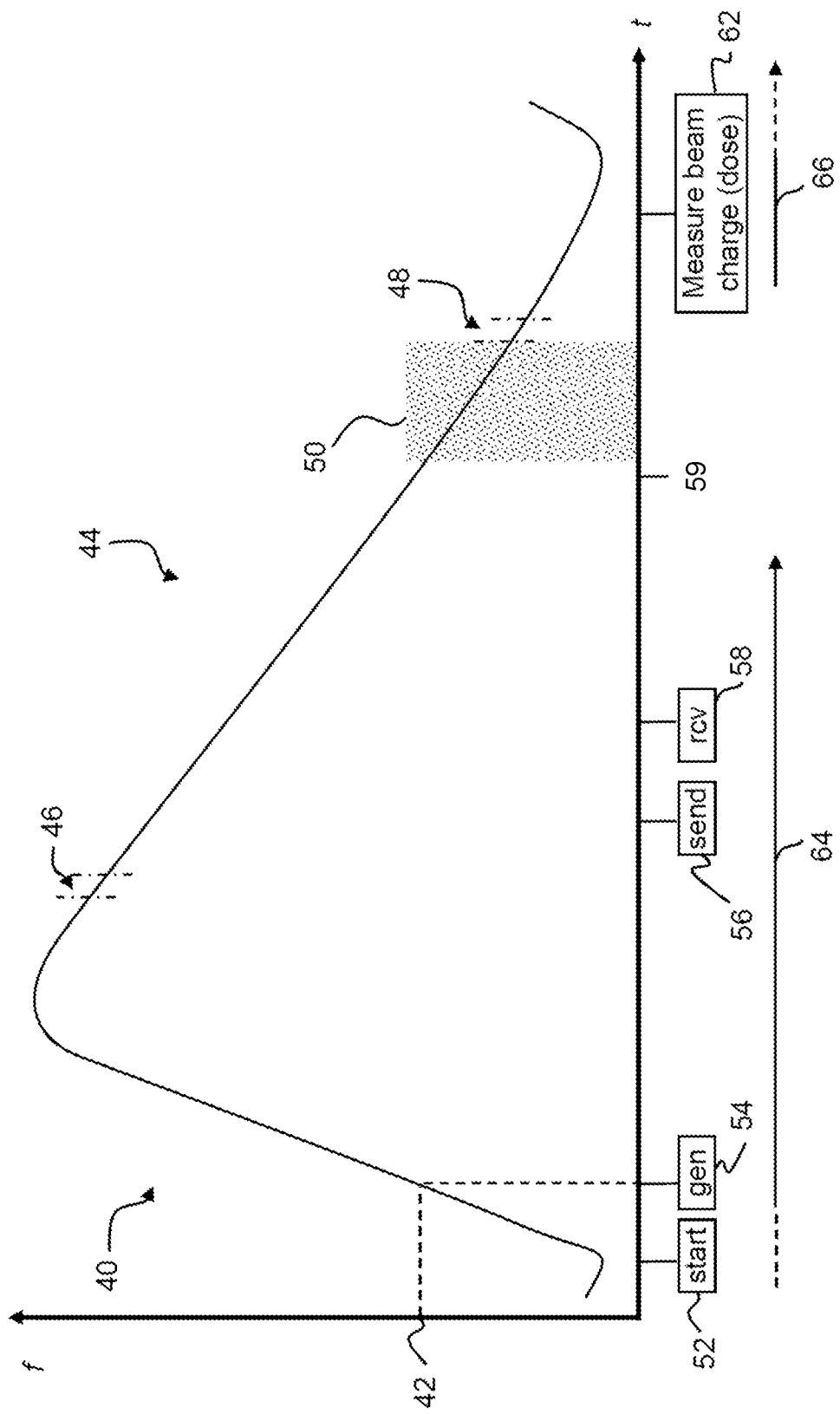
FIG. 3: depicts the frequency of the alternating voltage during one acceleration cycle superimposed with the workflow of a method according to an aspect of the invention.

FIG. 3 depicts in more details a workflow for extracting an ion beam pulse according to the embodiment of FIG. 1. The workflow described refers especially to the setting of the scanning magnets 22, although the procedure may be applied to other external or internal beam control elements. At the start of a new acceleration cycle at 52, the frequency of the alternating voltage applied between the Dees is increasing. In the meantime, the setting procedure 64 of the scanning magnets 22, in accordance with the treatment plan, has been initiated, preferably starting at a defined point in time, soon after the extraction of the previous pulse. When the frequency reaches the predefined value 42, a reference signal is generated at 54 by the reference signal generator and transmitted to the central control unit 24. At 56, the central control unit 24 sends a timestamp over the network 36 to the local control unit of the scanning magnets 22. The timestamp comprises the time at which the reference signal has been generated. After a small amount of time, the timestamp is received at 58 by the local control unit of the scanning magnets.

After receiving the timestamp, the local control unit of the scanning magnets registers the status of the scanning magnets and sends a signal over the network to the central control unit 24, the signal being representative of the registered status of the scanning magnets. The central control unit 24 verifies whether or not the setting, represented by the registered status, of the magnets complies with the setpoints. This assessment process is synchronized with the generation of the reference signal. In any embodiment of the invention (not only the one corresponding to FIGS. 1 and 3 and including network 36), this means that at least the time at which the status registration is performed is well-defined with respect to the time the reference signal is generated. This is possible because this latter time is communicated to the local control units of the beam control elements. These units can be programmed to perform the status registration at a predefined time starting from the reference signal generation. Alternatively, the message sent on the network (including the timestamp) may comprise also the time at which the control unit should register the status of the scanning magnets. The point in time when the status registration is performed and possibly also the point in time when the status signal is sent back to the central control unit 24 can be programmed in order to make sure that the assessment is terminated before the onset of the forbidden time zone 50

(for example at point 59 in FIG. 3). This is possible because the point in time at which the forbidden zone 50 begins, starting from the reference signal generation, is known (given that the reference signal generation defines a well-defined point of the cycle). Preferably a safety margin is taken into account, making sure that the assessment is terminated well before the forbidden zone 50.

If the required setpoints are reached for the scanning magnets and possibly for other external or internal control elements, the beam extraction proceeds. If it is not the case, the acceleration cycle is cancelled. The cancellation order is generated by the central control unit 24, before the onset of the forbidden time zone 50. The setting 66 of the scanning magnets for the next ion beam pulse starts just after the cancellation or in case the assessment is positive, after the extraction of the ion beam pulse. The measurement 62 of the beam intensity and dose by the ionization chamber 18 takes place after extraction of the beam pulse, at point 62. The result of this measurement may be applied to update beam control elements within the synchrocyclotron before extraction of the next pulse. In any embodiment of the invention, the reading of the output of the beam monitoring elements such as the ionization chamber 18 is equally synchronized with the reference signal, i.e. this reading step is performed at a well-defined point in time with respect to the generation of the reference signal.

In another embodiment of the invention that is not depicted in the accompanying figures, the reference signal generator is connected to each of the local control units of the internal, external beam control elements and beam monitoring elements, and to the central control unit 24 by a dedicated cable (e.g. by a coaxial cable). The reference signal 38 is generated and sent directly through the cables to the control units of the beam control and beam monitoring elements and to the central control unit 24. As the reference signal is received quasi-instantaneously by all the beam control and monitoring elements, the reference signal itself serves two purposes: synchronisation of the clocks of the control units and communicating the time at which the reference signal is generated. The control units of the beam control elements are thereby aware of this well-defined moment in the frequency cycle, and the assessment procedure can be synchronized with the reference signal, in the same manner as described in relation to the embodiment of FIG. 1.

In an alternative embodiment of the invention, the assessment of the status of the beam control elements is realized by the local control unit of the beam control elements. The generation and sending of the cancellation order is therefore delegated to the local control unit of the beam control elements. In the case a local control unit assesses that its beam control element does not comply with its setpoint, a cancellation order of the acceleration cycle is generated by the local control unit and transmitted by any appropriate means for transmitting the cancellation order (e.g. by a network or cables). The central control unit 24 (FIG. 1) monitors the whole irradiation process and may update the setpoints in order to comply with the irradiation plan.

The method of the invention may be applied to each pulse of ions accelerated in the synchrocyclotron. Alternatively, the method may be applied not to each pulse, but to selected pulses. For example, it is possible that the irradiation plan requires a large number of ion beam pulses in each voxel. For a first group of pulses, controlling whether or not the beam must be cancelled is therefore not mandatory because the beam pulses are in any case required. In order to relieve the network load, for example, the reference signal generator may thus be programmed not to generate a reference signal for the cycles initiated for producing said first group of pulses. When a given number of pulses has been directed at the voxel, the reference signal may then be generated for the subsequent pulses, until the required dose for the voxel has been reached.

Figure 4:
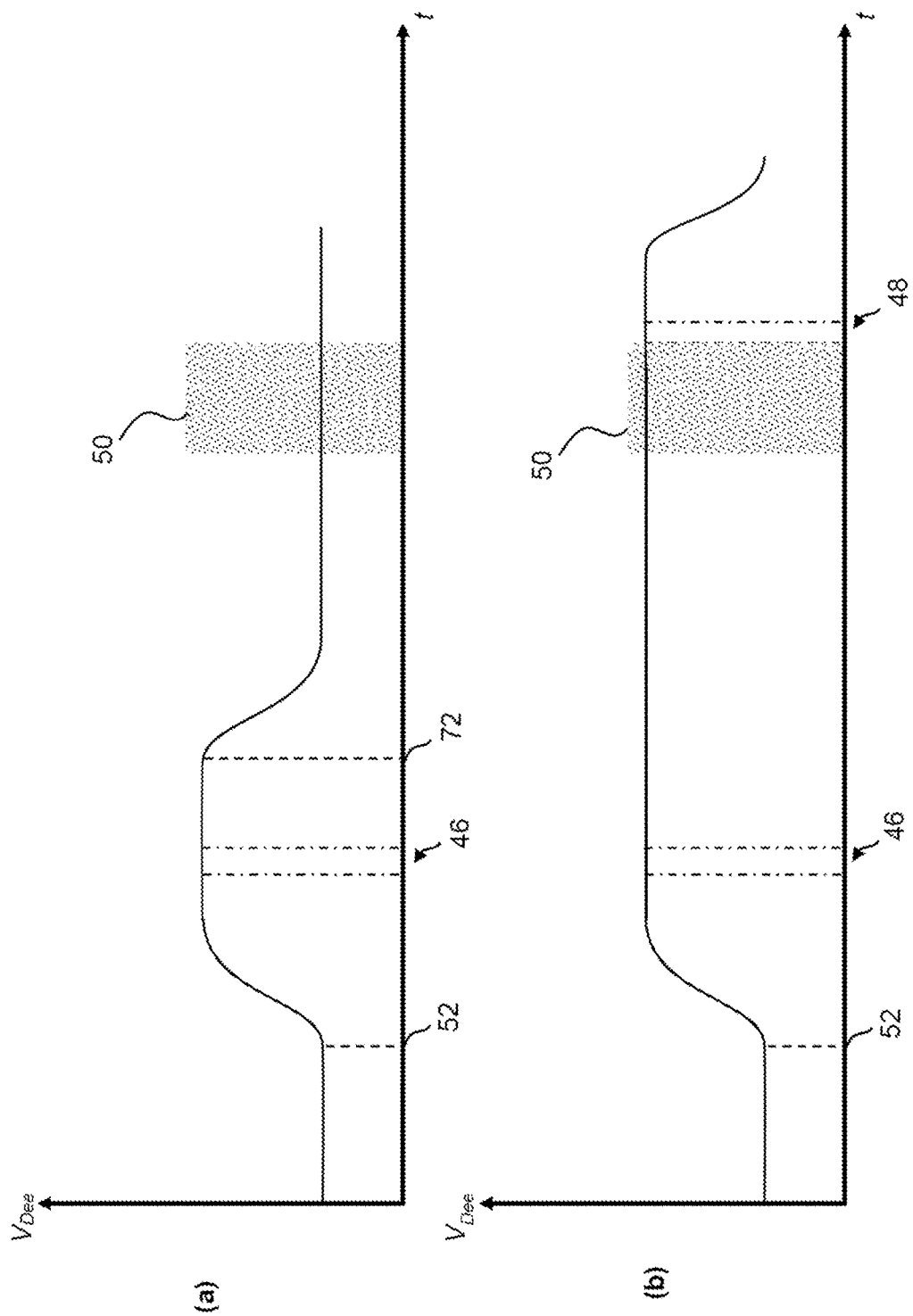
FIG. 4: depicts the magnitude of the alternating voltage between the Dees as a function of time.

According to a preferred embodiment, cancelling the extraction is done by lowering the Dee voltage. FIG. 4 has a two panel structure and shows the magnitude of the alternating voltage between the Dees as a function of time. The first panel (a) depicts the case where a cancellation order of the beam pulse is issued and the second panel depicts the case where no cancellation of the beam pulse occurs. At the start 52 of a frequency cycle, the synchrocyclotron increases the magnitude of the voltage between the Dees to a predefined value. After the charged particles have been captured during the capture window 46, the beam pulse can either be extracted and delivered to the patient (panel (b)) or cancelled (panel (a)) before the predefined time interval. The cancellation order 72 comprises lowering the magnitude of the voltage between the Dees to the initial value (i.e. the value at the beginning of the acceleration cycle). The voltage drop may last for approximately 30 µs. It has to be noted that the forbidden time interval 50 takes into account the time for the magnitude of the voltage between the Dees to drop. A cancellation order 72 issued just before the onset of the forbidden time interval 50 will result in a "clean" cancellation or stop of the ion beam pulse in preparation.

While specific embodiments have been described herein in detail, those skilled in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

The invention claimed is:

1. A method for controlling the extraction of ion beam pulses produced by a synchrocyclotron comprising electrodes configured to be placed in a magnetic field, wherein an alternating voltage is applied between the electrodes, and wherein the frequency of the alternating voltage is modulated in a cyclic manner, the method applying at least one of an energy degrader or a magnet, the method comprising:
   initiating an acceleration cycle of the synchrocyclotron to provide an ion beam pulse, wherein one modulation cycle of the modulated frequency of the alternating voltage corresponds to one acceleration cycle of the synchrocyclotron;
   generating a reference signal based on the modulated frequency of the alternating voltage during the acceleration cycle, the reference signal being generated when the frequency reaches a predefined value;
   communicating a timestamp identifying when the reference signal is generated, to the at least one of an energy degrader or a magnet;
   registering a status of the at least one of an energy degrader or a magnet after communicating the timestamp; and
   determining whether to extract an ion beam pulse based on the registered status of the at least one of an energy degrader or a magnet.

2. The method according to claim 1, wherein the method further comprises communicating the timestamp to one or more beam monitoring elements and wherein a reading of an the output of the one or more beam monitoring elements is equally synchronized with the timestamp.

3. The method according to claim 2, wherein the at least one of an energy degrader or a magnet is interconnected in a network, and wherein the step of communicating the timestamp further comprises sending the timestamp over the network, to the at least one of an energy degrader or a magnet and to the one or more beam monitoring elements.

4. The method according to claim 2, wherein the step of communicating the timestamp further comprises propagating the reference signal, over one or more cables, to the at least one of an energy degrader or a magnet and to the one or more beam monitoring elements.

5. The method according to claim 2, wherein the method further comprises operating the at least one of an energy degrader or a magnet, and wherein the one or more beam monitoring elements, is synchronized according to a common timeline.

6. The method according to claim 1, wherein the method further comprises assessing the registered status of the at least one of an enemy degrader or a magnet, and lowering the magnitude of the alternating voltage between the electrodes of the synchrocyclotron based on the assessment.

7. The method according to claim 1, wherein the frequency changes according to a cyclic pattern comprising a rising slope and a falling slope, and wherein the generation of the reference signal occurs when the frequency is on the rising slope.

8. The method according to claim 1, wherein the synchrocyclotron comprises a rotating capacitor for modulating the frequency of the alternating voltage applied between the electrodes.

9. The method according to claim 1, wherein the reference signal is generated when the frequency of the alternating voltage applied between the electrodes reaches a given value between 60 MHz and 92 MHz.

10. The method according to claim 1, wherein the reference signal is generated at selected cycles of the frequency of the alternating voltage.

11. The method according to claim 1, wherein the at least one of an energy degrader or a magnet comprises at least one energy degrader or magnet external to the synchrocyclotron.

12. The method according to claim 11, wherein the external energy degrader or magnet comprises at least a set of scanning magnets for directing the beam at one or more particular portions of a target.

13. An ion beam irradiation system configured to control the extraction of ion beam pulses by the method according to claim 1, the system comprising :

a synchrocyclotron;
at least one of an energy degrader or a magnet,
one or more beam monitoring elements,
a central control unit,
an antenna for detecting the frequency of the alternating voltage between the electrodes of the synchrocyclotron,
a reference signal generator.

14. The system according to claim 13, wherein the reference signal generator comprises :
a digital sampler, for sampling a signal produced by the antenna,
a computer for calculating the frequency of the alternating voltage based on samples provided by the digital sampler, wherein the computer is configured to calculate the frequency repeatedly during a frequency cycle of the modulated frequency, and
a controller for detecting when the calculated frequency is equal to a reference value, and for emitting the reference signal.

15. The system according to claim 13, wherein the at least one of an energy degrader or a magnet further comprises at least one of scanning magnets or guiding magnets.

16. The system according to claim 13, further comprising an actuator for positioning the at least one of an energy degrader or a magnet with respect to particular portions of a target.

17. The method according to claim 1, wherein assessing the registered status of the at least one of an energy degrader or a magnet further comprises comparing one or more measured values of the registered status to command values associated with beam control.

18. The method according to claim 17, the method further comprising proceeding with or cancelling an extraction of the beam pulse based on the comparison of the one or more measured values of the registered status to the command values.

19. The method according to claim 1, the method further comprising extracting the ion beam pulse when a required command value is reached, and measuring an intensity and dose of the ion beam pulse after extraction.

20. The method according to claim 1, wherein the acceleration cycle of the synchrocyclotron lasts between 0.5 ms and 1.5 ms.

* * * * *

UNITED STATES PATENT AND TRADEMARK OFFICE
CERTIFICATE OF CORRECTION

PATENT NO.        : 10,070,510 B2
APPLICATION NO.   : 15/725350
DATED             : September 4, 2018
INVENTOR(S)       : Gabriel Krier It is certified that error appears in the above-identified patent and that said Letters Patent is hereby corrected as shown below:

In the Claims

Claim 2, Column 10, Lines 65-66, "a reading of an the output" should read -- a reading of an output --.

Signed and Sealed this
Seventh Day of May, 2019

Andrei Iancu
*Director of the United States Patent and Trademark Office*